United States Patent [19]
Marcus

[11] Patent Number: 5,336,177
[45] Date of Patent: Aug. 9, 1994

[54] INTEGRAL PENETRATING SURGICAL DRAIN DEVICE

[76] Inventor: William Y. Marcus, 8912 Burdette Rd., Bethesda, Md. 20817

[21] Appl. No.: 54,070

[22] Filed: Apr. 29, 1993

[51] Int. Cl.[5] ............................................. A61M 31/00
[52] U.S. Cl. ...................................... 604/51; 604/264
[58] Field of Search ............... 128/760, 763, 764, 766; 604/8, 51, 46, 54, 35, 264, 280, 411, 53

[56] References Cited

U.S. PATENT DOCUMENTS

| | | | |
|---|---|---|---|
| 2,148,541 | 2/1939 | Dierker | 604/35 |
| 2,665,689 | 1/1954 | Butler | 604/272 |
| 2,777,443 | 1/1957 | Thomas et al. | |
| 2,833,281 | 5/1958 | Krug | 604/411 |
| 3,589,368 | 6/1971 | Jackson | 128/350 |
| 3,633,585 | 1/1972 | McDonald, Jr. | |
| 3,680,562 | 8/1972 | Wittes et al. | 604/51 |
| 3,854,477 | 12/1974 | Smith | 604/280 |
| 4,140,108 | 2/1979 | Nugent | 128/760 |
| 4,246,899 | 1/1981 | Loseff | 604/97 |
| 4,359,053 | 11/1982 | Benjamin | |
| 4,664,652 | 5/1987 | Weilbacher | 604/133 |
| 4,781,704 | 11/1988 | Potter | 604/270 |
| 4,801,297 | 1/1989 | Mueller | 604/280 |
| 4,883,474 | 11/1989 | Sheridan et al. | |

Primary Examiner—Jerome L. Kruter
Attorney, Agent, or Firm—Thomas P. Liniak

[57] ABSTRACT

An integral penetrating surgical drain device is taught that is formed of a flexible tube having a first imperforated end section, a second perforated end section, and a penetrating element mounted to the first end section, whereby the drain device may be used to exit the drain tube from the body cavity and through the body wall and to complete connection to a suction drain unit, without the necessity of removal or attachment of other elements to the drain device.

A method of emplacing an integral penetrating surgical drain device having a penetrating element and an integral tubular member with the diameter of the penetrating element being no greater than the diameter of the tubular member, within a body cavity, is also taught comprising the steps of placing a surgical drain, having a first imperforated section and a second perforated section formed thereto with a hollow needle mounted to the first section, within a surgical opening of a body cavity; inserting the hollow needle with the first imperforated end section out through the body wall; closing the surgical opening; and inserting the hollow needle mounted to the imperforated section into a suction unit.

11 Claims, 2 Drawing Sheets

INTEGRAL PENETRATING SURGICAL DRAIN DEVICE

FIELD OF THE INVENTION

The present invention relates to improved surgical drains and the methods of placing those surgical drains within a body cavity of a patient.

BACKGROUND OF THE INVENTION

Various surgical drain designs have previously been used to drain body cavities in connection with surgical procedures, and various methods of emplacing the drain tubing have been practiced in the past. Drain tubes are generally formed with a first imperforate hollow section and a second perforated hollow section having spaced drain holes that extend through its walls. It is known in the prior art to use a solid sharpened rigid rod or trocar sealed partially within and to an imperforate end of a tube or catheter to position a drain tube within a body cavity, such as shown in U.S. Pat. No. 4,883,474 to Sheridan. The trocar is swaged or press fit into the hollow tube to form an integral connection therewith.

After insertion into the body, the trocar with the imperforate section of tubing is passed from the body cavity through the body wall to a position wherein the rod or trocar and a portion of the imperforate section extend away a distance from the body and the perforated section remains inside the body wall. The outwardly extending portion of the imperforate section of tube is then severed at a location near the trocar and the severed trocar is disposed of. The resulting imperforate section of tube (or catheter) is then secured to an appropriate additional vacuum drain device to complete assembly of the suction type drain device.

Alternatively, use of a sharpened hardened plastic end on a flexible catheter tube, to permit body penetration by the hardened end, is illustrated in Sheridan U.S. Pat. No. 4,883,474. Once body penetration is achieved by this device, the hardened sharp end is severed to permit the catheter tube to be connected to a suction drain device by use of an additional structure.

A catheter having a plurality of drain openings for use within body openings is illustrated in U.S. Pat. No. 4,801,297 to Mueller, which discloses a multitude of radially spaced, axially aligned slits and spaced round perforations that extend through the catheter wall. U.S. Pat. No. 3,633,585 to McDonald, Jr., U.S. Pat. No. 3,854,477 to Smith, and U.S. Pat. No. 3,680,562 to Wittes, et al also teach the use of spaced round holes that extend through the catheter walls.

Several techniques have been utilized to achieve the mounting of drain catheters to solid metallic trocars or other similar devices to enable body wall penetration including bonding with resins or swaging, as disclosed in U.S. Pat. No. 3,680,562 to Wittes, et al., or U.S. Pat. No. 2,665,689 to Butler. It is also known to join silicone or plastic tubing over a smooth metal element by selecting a diameter for the plastic tubing that is capable of a degree of classic expansion to enable it to slide over the metal tubing to form a relatively firm connection.

Prior to the present invention, the positioning of a perforated section of a drain device or catheter within a patient's body, while having an imperforate extension of the catheter connected to an external drain system, involved in the steps of sealing a heavy metal cutting tool or trocar partly within the imperforated end of a flexible catheter or drain device, inserting a heavy metal cutting tool and catheter into a surgical opening, puncturing the body cavity wall to move the cutting tool and a portion of the imperforate section to a position extending outside of the body, severing and discarding the end of the catheter or drain device containing the heavy metal cutting tool, assembling an additional separate connecting device to the imperforate end of the catheter or drain device and then joining the connecting device to a suction unit.

The emplacement of existing surgical drain systems requires numerous steps, including the use of a separate device in addition to the drain device, the removal of the cutting device from the drain and then coupling the altered drain to a hollow connecting device. The additional structure and number of steps required by existing systems, to accomplish the same end result, likewise increase the risk of accidental puncture by contaminated sharpened devices as well as increasing the cost of the drain unit. The use of a heavy metal cutting tool, trocar or similar device, to form a perforation through the body cavity wall of a much larger diameter than the diameter of the catheter, creates an additional opening, of a size considerably larger than the diameter of the drain tubing itself, through the body wall, in the area of the surgical procedure. This, in effect, is an unnecessary size opening since in existing devices, the trocar has no function other than perforating the body, and is subsequently removed and discarded.

SUMMARY OF THE INVENTION

The present invention overcomes these complexities and problems presented by the prior art. It provides an integral penetrating surgical drain device that does not require any additional devices or structures in order to accomplish insertion and positioning of the drain device partially within the body of a patient, and also connection to a vacuum type drain element. The present invention realizes all of the important advantages while at the same time allowing the user a choice of different size penetrating elements. As a result, diameter of the hole created in the body cavity to position the device is no larger than and perhaps smaller than the diameter of the required drain device. Additionally, the cost saving and safety that results in the present invention from not having to disconnect a penetrating element from the drain and subsequently reconnect another additional element offer a marked improvement over prior art devices, in terms of simplicity, cost and safety. The present invention comprises a hollow needle or trocar internally connected to and contained partly within an imperforate section of a drain unit that also has an extended perforated drain section intended to remain inside the body when properly positioned.

The device of the present invention is initially placed inside the wound and then is exited by urging the penetrating element against and then through the body cavity wall of a patient until only the perforated section of the drain remains within the cavity, while cutting only a minimal opening through the body wall. After exiting the body wall, the penetrating element attached to the drain device may be immediately inserted through the elastomer seal of a suction unit without the use of an additional connecting device.

Accordingly, it is an object of the present invention to avoid the extended procedure required by past surgical drain systems of providing a special solid cutting tool on the first section of the drain device, passing a portion of the new combined device out through the body wall, severing the first section of the drain device having the special solid cutting tool, mounting a separate additional hollow connecting device onto the severed end of the drain device, and then inserting the hollow connecting device into a suction unit.

Another object of the present invention is to provide a surgical drain device that utilizes either a hollow trocar or a needle as the penetrating element. A further object of the present invention is to provide a drain device with an integral penetrating member that requires a puncture through the body wall of a diameter no greater than, and in some cases, less than that of the drain tube.

An object of the invention is to provide a new and improved unitary penetrating surgical drain device which requires no further assembly or disassembly once it has been positioned in a body cavity in order to connect it to a suction device. Still another object of the present invention is to provide a dual surgical drain device having an elongated elastomeric tube with a central section having a plurality of spaced perforations or drain holes and first and second imperforate sections located on each end respectively of the central section with hollow penetrating elements securely mounted to the outer ends of each of the imperforated sections, such that the special surgical drain unit may, at the time of use, be severed at a desired location in the perforated section to form two complete surgical drain devices.

Yet another object of the present invention is to provide a simplified process of placing a surgical drain device having a penetrating element secured to a hollow imperforate first end section and a perforated second end section through a surgical opening within a body cavity, then inserting the hollow needle and the first end section of the drain device out through the body cavity wall and away from the surgical opening, thus leaving the perforated section within the body cavity, and then inserting the needle, which is still attached to the imperforate section of the drain device into a suction unit, to complete the suction drain from the body cavity.

These and other objects of the present invention are satisfied by a surgical drain device for emplacement in a body cavity, comprised of an integral flexible tube having a first end section and a second end section; said first end section comprising imperforate tubular walls; said second end section comprising tubular walls with spaced perforations therein; and a substantially hollow penetrating element partly within and mounted to said first section, said penetrating element having a diameter no greater than the diameter of said flexible tube.

The advantages and objects of this invention may be best understood by reference to the following description taken in conjunction with the accompanying drawings, in which like reference numerals identify like elements in the Figures.

DETAILED DESCRIPTION OF THE PREFERRED EMBODIMENTS

The present invention provides a significant improvement over known surgical drain devices and methods of emplacement of those drain devices. The invention reduces the required size of the body wall perforations normally resulting from using a heavy sharpened trocar to place a drain device inside a patient and exit a portion of the device through a patient's body cavity. It also simplifies the steps of emplacing a surgical drain device within a body cavity, and subsequently connecting it to a suction drain unit and eliminates need for additional structural elements.

Figure 1:
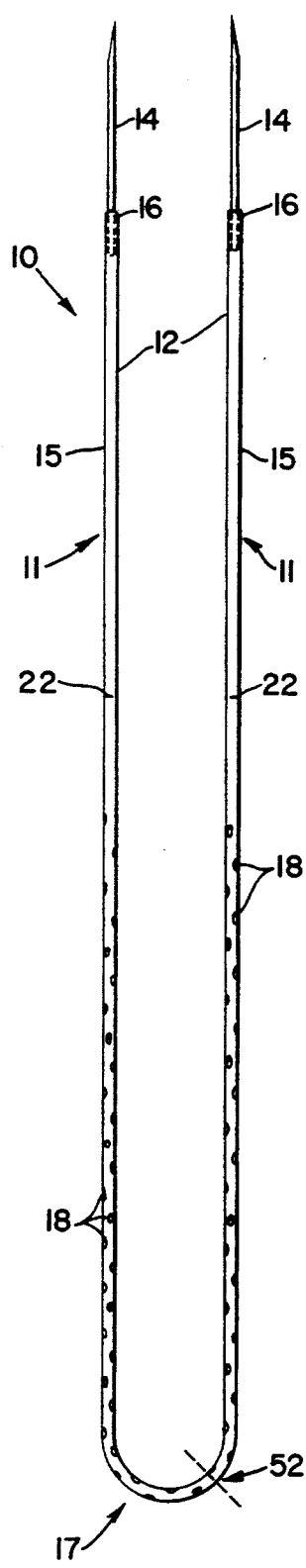
FIG. 1 is a plan view of one embodiment of the improved surgical drain device, according to the present invention, which may be severed to form two complete penetrating surgical drain devices.
Figure 2:
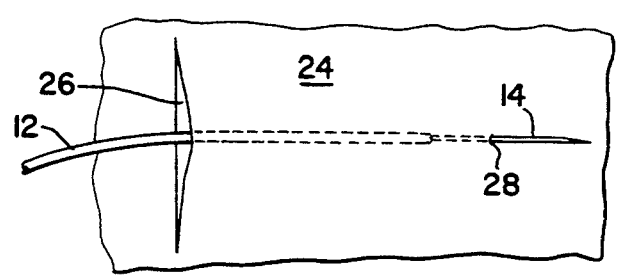
FIG. 2 is a fragmented side view of the one embodiment penetrating surgical drain device of the present invention, illustrating insertion through a surgical opening within a patient and its subsequent exit out through the body wall.
Figure 3:
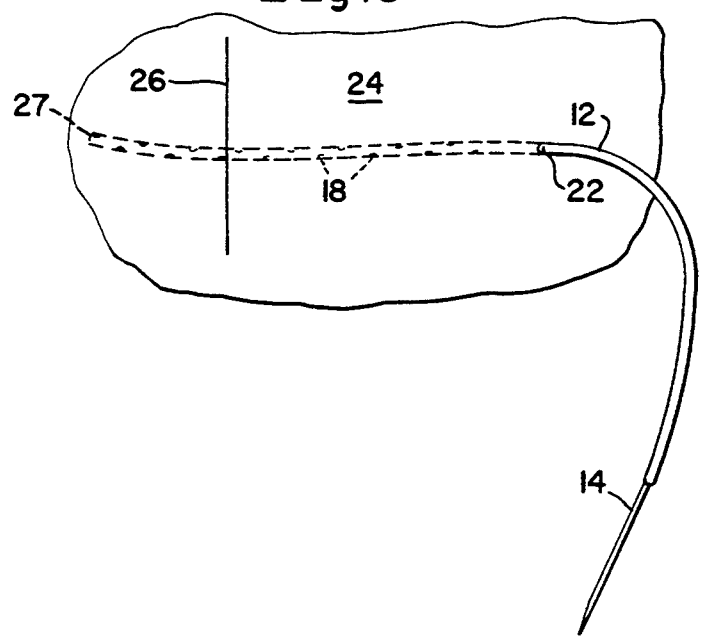
FIG. 3 is a side view of one embodiment of the present invention with the drain device partially out of the body, so that only the perforated section of the drain device remains within the body cavity.

Referring to the embodiment illustrated in FIGS. 1-3, dual penetrating surgical drain device 10 which is comprised of two complete drain devices 11 that are severed at a line such as line 36. Severing point 36 is determined by the length of perforated drain section 17 desired to be left in the body. Each of drain devices 11 is formed from a flexible hollow catheter 12 having a drain section 17 with spaced perforations or drain holes 18. A hollow needle 14, preferably of metallic construction such as stainless steel is inserted into the imperforated end section of drain device 11 and mounted to or swaged at end 16 to form a firm, substantially airtight connection to the end 16.

The spaced perforations of the drain section 17 extend for a distance sufficient to provide proper drainage from drain device 11 when emplaced within a body cavity. Drain holes 18 are preferably set forth as a series of offset rows of perforations located around the periphery of drain section 17 of catheter 12. Holes 18 are therefore staggered 90° as you traverse the outer circumference of drain section 17 of device 11. Although their size varies according to the end use of device 11, drain holes 18 from each row are preferably spaced approximately 7-8 mm apart and are about 1 mm in diameter.

Figure 4:
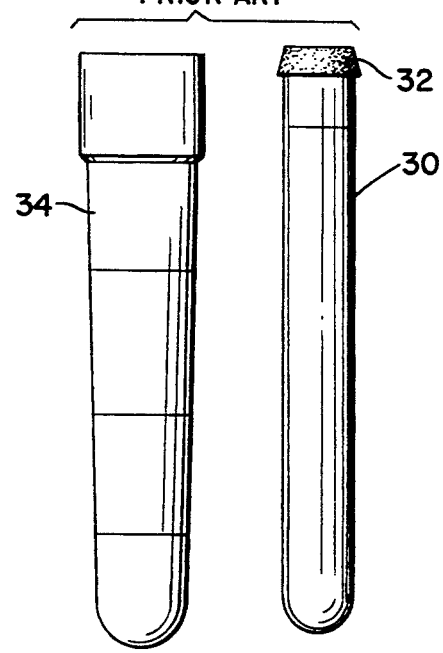
FIG. 4 discloses a typical tubular evacuated sealed test tube which may be used in conjunction with the present invention as a suction withdrawal unit.

Imperforate section 15 of the drain device 11 is of a length sufficient to permit needle 14 to exit from the body and to be inserted into an external suction unit 30 such as shown in FIG. 4. Dual needle drain device 10 may be packaged as a sterile unit which merely requires severing at desired zone 36 of the perforated drain section 17 of dual drain device 10 prior to use according to the type and requirement of the drain needed or as a ready to use pre-severed device such as 11. Device 11 may also be packaged in preserved form. Guide marks 22 may be positioned at desired locations along the catheter 12 to assist in proper positioning of the drain section 17 of device 11 within the body cavity. Referring to FIG. 2, since sharpened hollow needle 14 is mounted to or swaged to drain device 11, the penetrating movement of drain device 11 as it is exited out through the body wall of a patient 24 results in making an opening in the body wall of a diameter less than that of needle 14 and no greater than that of catheter 12 to accomplish this purpose.

The procedure of using the surgical drain device 11 of the present invention within a patient having an initial surgical opening, such as that illustrated at 26 in FIG. 2 of the drawings, is now described in more detail. This procedure first requires severing the dual drain device 10 at a location such as 36 within perforations, such that a predetermined length of the perforated section 17 is provided for the particular use of drain device 11. The end 16 of drain device 11 containing hollow needle 14 is then inserted into surgical opening 26 through the body cavity, and a short distance from surgical opening 26, needle 14 of drain device 11 is moved against and then out through the body wall at location 28, as shown in FIG. 2 of the drawings.

As shown in FIG. 3, needle 14 and a length of imperforated section 15 of device 11 are then further drawn out of the body cavity until proper guide marks 22 are exposed at opening 28, or in the absence of marks 22, the proper length of drain section 17 are left in the body of patient 24 to act as a drain and the proper length of imperforate section 15 has been removed. Once the remainder of the end 27 of drain device 11 is completely drawn through surgical opening 26 and is positioned within the body cavity, surgical opening 26 may then be closed using standard surgical procedures. The final position of drain device 11 in a body cavity of a patient 24 is illustrated in FIG. 3.

To complete assembly of the surgical drain from the patient, needle 14 of drain device 11 is then pushed through elastomeric seal 32 on evacuated tube drain unit 30 so as to puncture seal 32, to initiate the suction through the entire drain device 11. Suction drain unit 30 is then encased within outer protective tube 34. Evacuated tube drain unit 30 can be any of a variety of such devices of different capacities, commonly available, that are sterile and are sealed so as to create a vacuum when connected to drain device 11. A preferred unit for this particular invention is sold under the trademark Vaccutainer by Bectar Dickinson Vaccutainer Systems.

The improved method of placing drain systems, in accordance with the present invention, eliminates the need to mount a heavy solid trocar onto drain device 11, the need to cut off the trocar after penetration out of the body cavity of a patient 24, and the subsequent need of mounting an additional separate connection device to the end of drain device 11 after the trocar has been cut off and prior to connecting drain device 11 to a suction drain unit. Additionally, the puncturing of the body wall accomplished by needle 14 results in an opening 28 in a body wall being created that is smaller in diameter than catheter 12.

Figure 5:
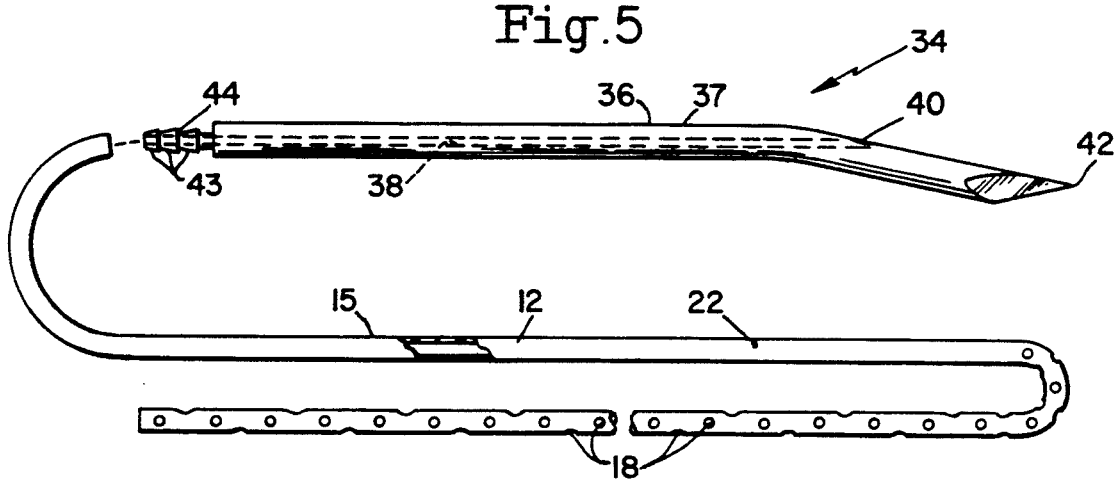
FIG. 5 is a plan view of another embodiment of the improved drain device of the present invention that utilizes a hollow trocar as a penetrating element.

A second embodiment of the present invention will now be described in detail with particular reference to FIGS. 5–7. Alternative drain device 34 utilizes the same catheter 12 with its imperforate section 15, spaced drain holes 18 and guide markings 22 as the embodiment illustrated in FIGS. 1–3. Likewise, device 34 is designed to be used in conjunction with an evacuated tube drain unit 30 as also described previously. Alternative device 34 features a hollow trocar 36 as a penetrating element instead of the needle 14 of the previously described embodiment.

In this embodiment, the superior ability of a trocar 34 to pierce the body wall is retained in a drain system that also utilizes the trocar 36 to pierce the evacuated tube drain and connect it to catheter 12 without the use of an additional connecting device. Alternative drain device 34 of this embodiment utilizes hollow trocar 36 having a penetrating point 42 located at one end and a catheter connecting means 44.

Trocar 36 is preferably constructed of stainless steel, aluminum or like material. Aperture 40 is located intermediate the ends of trocar 36, preferably closer to the end of trocar 36 with penetrating point 42. Aperture 40 leads to channel 38 that extends within trocar 36 from aperture 40 through the end of catheter connecting means 44. Diameter of channel 38 is substantially the same size as inner diameter of catheter 12. Trocar 36 is connected to catheter 12 by inserting catheter connecting means 44 into a portion of imperforate section 15 of catheter 12, in a manner to form a substantially airtight seal between catheter 12 and trocar 36. This connection is facilitated by multiple angled stops 43 located on connecting means 44, which, due to their angled construction, facilitate insertion of trocar 36 into catheter 12 and resist removal of trocar 36 from catheter 12.

Figure 6:
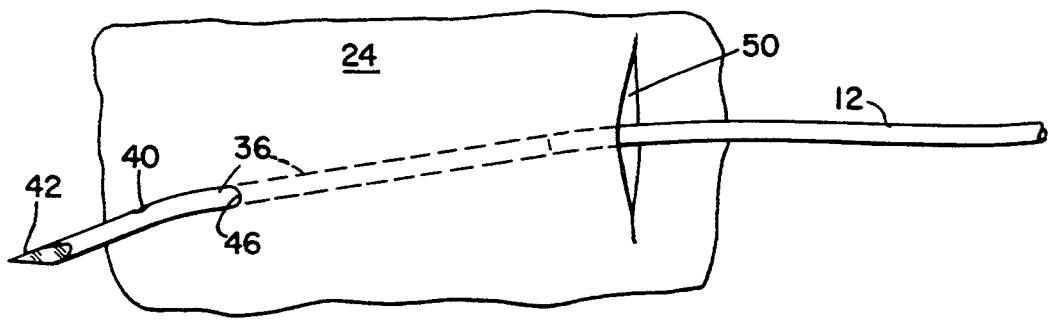
FIG. 6 is a fragmented side view of the FIG. 5 embodiment of the present invention illustrating that method of insertion of the device through a surgical opening and its subsequent exit through the body wall.
Figure 7:
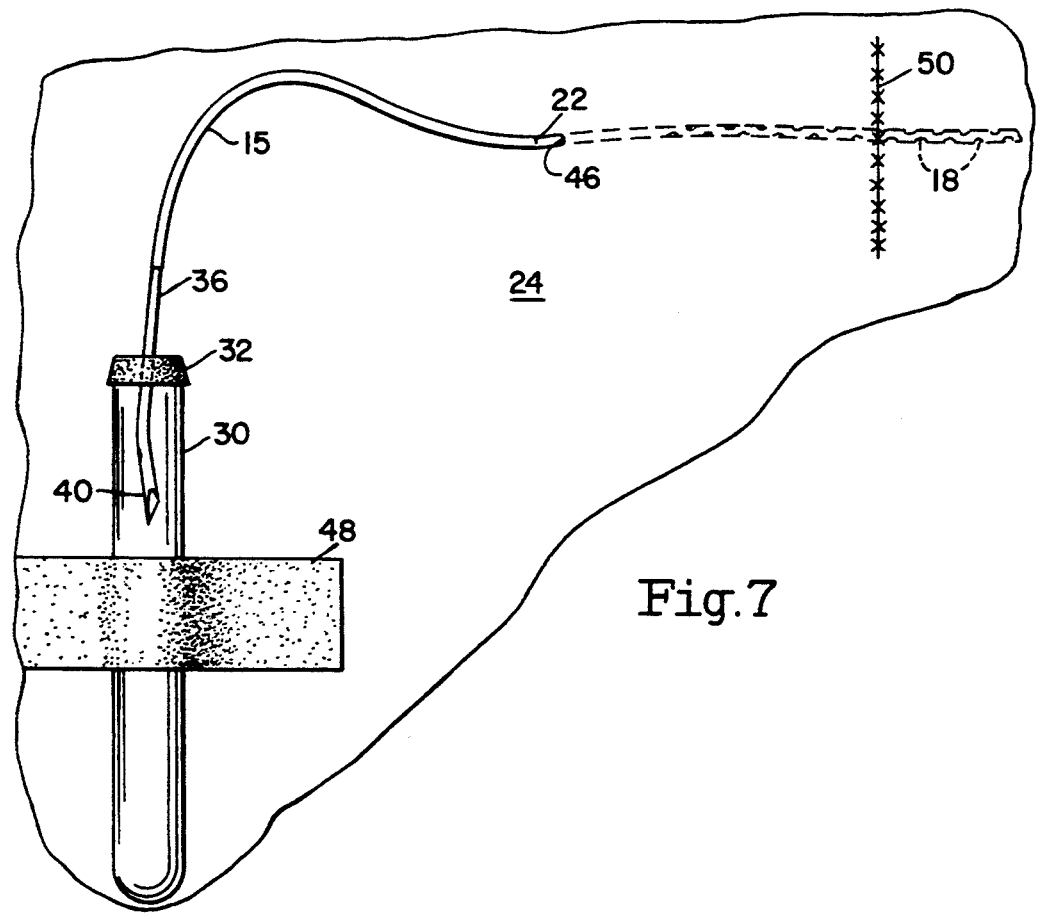
FIG. 7 is a partial x-ray view of the FIG. 5 embodiment of the present invention illustrating the drain device in its final position connected to an evacuated tube drain unit.

As illustrated in FIG. 6, alternative device 34, featuring hollow trocar 36, is connected to catheter 12 inserted in an existing surgical opening 50 of a patient 24 and exited through an opening 46 in the body wall made by trocar 36. End of device 34 with trocar 36 continues to be pulled outside of the opening 46 until such time as the entire perforated section 17 is positioned within the body and a sufficient length of imperforate section 15 of catheter 12 extends outside the body wall. As illustrated in FIG. 7, device 34 is then connected to a typical evacuated tube drain unit 30 such as previously described. Drain unit 30 is then secured to patient 24 by using adhesive strip 48 or like mechanism. Hollow trocar 36 must be inserted a sufficient distance into evacuated tube system 52 to insure that opening 40 in trocar 36 is entirely within tube in order to form a vacuum through channel 40 of trocar 36, imperforate section 15 and perforated section 17 now located within body cavity in close proximity to prior surgical opening 50.

It is understood that the invention may be embodied in other specific forms without departing from the spirit or inventive characteristics thereof. The present examples and embodiments, therefore, are to be considered in all respects as not restrictive but illustrative, and the invention is not limited to the details given herein.

I claim:

1. A flexible drainage device consisting essentially of:
    a flexible tube having a substantially constant diameter along its entire length, first and second end sections, and an intermediate zone between said end sections;
    said intermediate zone of said tube having spaced perforations for draining of body fluids;
    a first hollow penetrating element having a main body with a substantially constant diameter along its entire length and a piercing element at one end, said main body being partly within and connected to said first end section of said flexible tube;
    a second hollow penetrating element having a main body with a substantially constant diameter along its entire length and a piercing element at one end, said main body being partly within and connected to said second end section of said flexible tube;

said first and second penetrating elements each having a diameter no greater than and substantially the same as the diameter of said flexible tube along their entire lengths; and severing line means in said intermediate zone of said tube to allow for plural drainage devices to be formed from said flexible drainage device.

2. The device of claim 1, wherein, said first and second penetrating elements are needles.

3. The device of claim 1, wherein, said flexible tube further comprises identifying marks thereon.

4. The device of claim 1, wherein, said perforations for draining of body fluids are spaced equidistantly about said tube.

5. A method of utilizing the surgical drain device of claim 1, comprising the steps of:

providing said drainage device; and severing said device at said severing point means to form first and second drainage devices out of said flexible drainage device.

6. The method of claim 5, further comprising the steps of:

placing said first surgical drainage device into a body cavity through a surgical opening with said first penetrating element leading the placement of said drainage device;

piercing the body wall with said first penetrating element;

moving said first penetrating element and a portion of said flexible tube through the body wall;

closing said surgical opening with said spaced perforations of said flexible tube retained in the body cavity; and inserting said first penetrating element into a suction drain unit by piercing said drain unit with said first penetrating element, thereby creating a partial vacuum in said first drainage device between said drain unit and the body cavity.

7. A combination body wall penetrating and surgical drain device consisting essentially of:

a flexible tube having a substantially constant diameter along its entire length and proximal and distal end sections and an intermediate zone between said end sections;

said intermediate zone of said tube having spaced perforations for draining of body fluids;

an integral substantially hollow penetrating element partly within and mounted to said proximal end section of said flexible tube, said element having a main body and a piercing member at one end;

said main body having a substantially constant diameter along its entire length; and said penetrating element having a constant diameter no greater than and substantially the same as the diameter of said flexible tube.

8. The device of claim 7, wherein, said penetrating element is a needle.

9. The device of claim 7, wherein, said flexible tube further comprises identifying marks thereon.

10. The device of claim 7, wherein, said perforations of said tube are spaced equidistantly about said tube.

11. A method of utilizing the device of claim 7, comprising the steps of:

placing said drain device into a body cavity through a surgical opening with said penetrating element leading the placement of said drain device;

piercing the body wall with said penetrating element;

moving said penetrating element and a portion of said flexible tube through the body wall;

closing said surgical opening with said spaced perforations of said flexible tube retained in the body cavity; and inserting said penetrating element into a suction drain unit by piercing said drain unit with said penetrating element, thereby creating a partial vacuum in said device between said drain unit and the body cavity.

* * * * *